United States Patent [19]
Chiesi et al.

[11] Patent Number: 5,538,968
[45] Date of Patent: Jul. 23, 1996

[54] GENESERINE DERIVATIVES PROCESSES AS CHOLINESTERASE INHIBITORS

[75] Inventors: Paolo Chiesi; Maurizio Del Canale; Vittorino Servadio; Eleonora Ghidini, all of Parma, Italy

[73] Assignee: Chiesi Farmaceutici S.p.A., Parma, Italy

[21] Appl. No.: 193,154

[22] PCT Filed: Aug. 4, 1992

[86] PCT No.: PCT/EP92/01762

§ 371 Date: Mar. 3, 1994

§ 102(e) Date: Mar. 3, 1994

[87] PCT Pub. No.: WO93/03041

PCT Pub. Date: Feb. 18, 1993

[30] Foreign Application Priority Data

Aug. 9, 1991 [IT] Italy .................. MI91A2237

[51] Int. Cl.[6] .................. C07D 265/02; A61K 31/535
[52] U.S. Cl. .................. 514/229.8; 544/663
[58] Field of Search .................. 544/63; 514/229.8

[56] References Cited

FOREIGN PATENT DOCUMENTS

| | | |
|---|---|---|
| 154864 | 9/1985 | European Pat. Off. . |
| 298202 | 1/1987 | European Pat. Off. . |
| 2374908 | 7/1978 | France . |

OTHER PUBLICATIONS

Robinson et al, Journal of Pharmacy and Pharmacology, 1968, 20S, 213S–217S.
Ligny et al, Chemical Abstracts 90: 162,308, abstract of French Patent FR 2 374 908 issued Jul. 1978.
Shishido et al, Journal of chemical Society, Perkin Trans., 1(11), Nov. 1987, 2491–2495.
Robinson et al., Journal of the Chemical society, Section C: Organic Chemistry, No. 15, 2077–2078, 1970.

*Primary Examiner*—Mukund J. Shah
*Assistant Examiner*—Matthew V. Grumbling
*Attorney, Agent, or Firm*—Bucknam and Archer

[57] ABSTRACT

Geneserine homologs of formula I

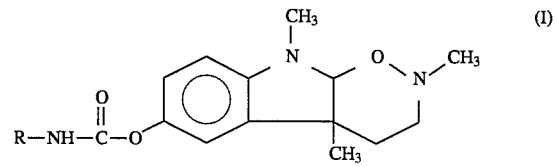

in which R is a straight or branched $C_2$–$C_{20}$ alkyl group, a $C_3$–$C_7$ cycloalkyl group, an unsubstituted phenyl or benzyl group, or a phenyl or benzyl group substituted by a $C_1$–$C_4$ alkyl group, a halogen atom or a $C_1$–$C_4$ alkoxy group, or a salt with an organic or inorganic non-toxic acid, exhibit anticholinesterase activity and may be useful in the treatment of Alzheimer disease and other conditions due to a neurological deficiency.

7 Claims, No Drawings

GENESERINE DERIVATIVES PROCESSES AS CHOLINESTERASE INHIBITORS

This is a 371 of PCT/EP92/01762 filed Aug. 9, 1992.

The present invention relates to geneserine derivatives, a process for the preparation thereof and pharmaceutical compositions containing them.

The compounds of the invention have the following general formula I:

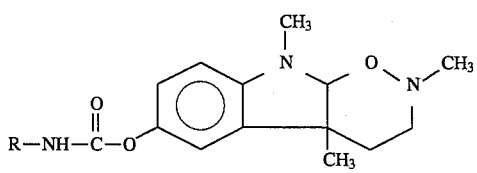

wherein R is a straight or branched $C_2$–$C_{20}$ alkyl group, a $C_3$–$C_7$ cycloalkyl group, a phenyl or benzyl group, optionally substituted with $C_1$–$C_4$ alkyl groups, halogen atoms, $C_1$–$C_4$ alkoxy groups.

Preferably R is an alkyl group having 4 to 12 carbon atoms, most preferably 6 to 8 carbon atoms.

Compound I, in which R is an n-heptyl group, is particularly preferred.

The invention also comprise s the salts of compounds I with pharmaceutically acceptable acids, particularly hydrochloric, sulfuric, tartaric, succinic, maleic, citric, methanesulfonic, fumaric, acetic, lactic, salicylic acids.

The compounds of formula I and the pharmaceutically acceptable salts thereof have inhibiting activity against cholinesterase and they can usefully be administered to patients suffering from Alzheimer disease or from various other conditions deriving from a neurologic deficiency.

Alzheimer disease is a form of progressive dementia clinically characterized by loss of memory and impairment of the intellective activities.

The importance of the cholinergic system in Alzheimer disease is well known and the loss of the cholinergic function has been found to be related to both the presence of neuropathologic lesions and a severe loss of the cognitive functions.

On the basis of such evidences, one of the most studied therapeutical approaches is the cholino-mimetic one, intended to improve and increase the cholinergic activity.

The most promising results were obtained using cholinesterase inhibitors, particularly physostigmine and tacrine.

EP-A-0154864 and EP-A-0298202 disclose physostigmine derivatives characterized by an increased lipophilia, due to the presence of long-chain alkyl or aryl residues on the carbamoyl group which is typical of this class of alkaloids.

Geneserine, even though it has been known for many years as an anticholinergic agent and used in therapy as a gastrointestinal antispastic, has never been the object of studies in order to verify its capability to restore the cholinergic function at the level of central nervous system.

Now it has been found that geneserine derivatives of formula I have pharmacological properties which are particularly interesting and advantageous compared with the prior art compounds.

Compounds of formula I can be prepared by oxidizing compounds of formula II

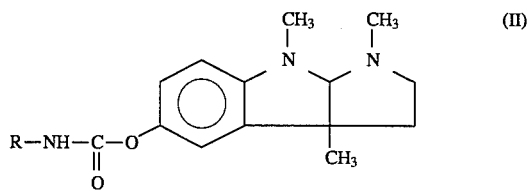

wherein R is as defined above.

The oxidation is preferably carried out by means of organic peracids or peroxides, such as m-chloroperbenzoic acid, monoperphthalic acid, peracetic acid, hydrogen peroxide, in inert solvents such as halogenated hydrocarbons, aromatic hydrocarbons, dimethylformamide, dimethylsulfoxide.

The preparation of compounds of formula II from physostigmine is known from EP-A-0154864 and EP-A-0298202, cited above.

Alternatively, compounds I can be obtained starting from geneserine by hydrolysis of the methylaminocarbonyloxy group and subsequent O-acylation with reagents capable of introducing the desired function

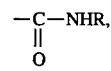

wherein R is as defined above.

Examples of acylating reagent s which can conveniently be used for this purpose comprise alkylisocyanates of formula R-NCO, wherein R is as in formula I, or in alternative substituted imidazolureas of formula III

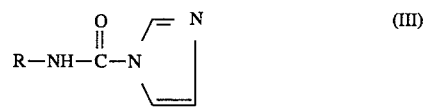

which can be prepared from carbonyldiimidazole and amines of formula $RNH_2$, wherein R is as defined above.

Hydrolysis of geneserine can be carried out analogously to that of physostigmine, by reaction with alkali alkoxides, whereas the O-acylation with the substituted imidazolureas is carried out in a strictly anhydrous medium, in the presence of metal sodium.

The resulting compounds I can then be salified with organic or inorganic non-toxic acids, according to the conventional techniques. Compounds I, for the envisaged therapeutical uses, will be formulated according to conventional techniques and excipients, such as those described in Remington's Pharmaceutical Sciences Handbook, Mack Pub. Co., New York U.S.A., $18^{ma}$ Ed. The average daily dosage will depend, of course, on many factors, but generally it will range from 10 to 1000 mg of compounds I or the salts thereof.

The following examples further illustrate the invention.

EXAMPLE 1 a) Eseroline.

To a solution of 5 g of eserine (Sigma or Fluka) in degased anhydrous ethanol (600 ml), 0,4 g of sodium are added portionswise. After about half an hour, solvent is evaporated off under vacuum at 30° C. and the resulting oil is treated with a 10% HCl solution and extracted with 3×50 ml of $CHCl_3$.

The combined organic phases are then washed with NaCl-saturated water until the red coloration in the aqueous phase disappears. After drying over $Na_2SO_4$ and evaporation under vacuum at 25° C., an oil is obtained, which is recrystallized from ½ ethyl acetate/petroleum ether, to obtain a solid in a 64% yield (2,54 g).

TLC: $CHCl_3/CH_3OH$=4/1 Rf=0,4 Developer: UV, phenol reactive

M.p.=126° C. (lit. 129° C.)

The obtained solid is stored as the hydrochloride; the base is treated with an hydrochloric EtOH solution to acid pH and evaporated under vacuum at 35° C.

M.p.=150°–151° C. (lit. 154° C.)

MS and NMR in conformity.

b) N-heptyl-imidazole-urea.

To a solution of 10 g of carbonyldiimidazole in 600 ml of anhydrous tetrahydrofuran, cooled at +5° C. and under strong stirring, a solution of 7,1 g of heptylamine in 40 ml of anhydrous tetrahydrofuran is added. After 45 minutes the solution is evaporated under vacuum at 30° C. and the obtained oil is treated with 2×70 ml of hexane, decanted and used directly for the subsequent reaction.

TLC: ethyl acetate/hexane=3/7 Rf=0,3 Developer: phenol reactive (green spot)

MS and NMR in conformity.

c) N-heptyleserine.

0,1 g of sodium are added to a solution of the product obtained according to a) (5 g) in 150 ml of degased anhydrous ethyl ether, under stirring and nitrogen atmosphere, and the mixture is left to react for 1 hour at room temperature. Then the product obtained in b) (4,5 g) is added to the reaction mixture, during half an hour. After a day at room temperature, the ether solution is washed with 50 ml of water, dried over $Na_2SO_4$ and evaporated under vacuum at 30° C.

The product is purified by F.C. (eluent ethyl acetate: 3=hexane: 1=methanol: 1; Rf=0,35; stationary phase: silica gel, 30–60 μm)

An oily product is obtained, in a 53% yield (4,16 g).

NMR in conformity.

Purity >90%

The product is stored as tartrate.

MS, $^1H$- and $^{13}C$-NMR in conformity.

d) N,heptyl-geneserine.

To a solution of 0,52 g of the product obtained in c) in 50 ml of degased chloroform, cooled to about 0° C., 0,7 g of m-chloroperbenzoic acid of 99% purity (by iodometric titration, after treatment according to Schwarts and Blungers, J. Org. 29, 1976 (1964)) dissolved in 10 ml of chloroform, are dropped into the reaction mixture keeping the temperature from 0° to 5° C. After that, the reaction is left at room temperature under stirring overnight. When the reaction is over, the chloroform solution is washed with 50 ml of a $NaHCO_3$ saturated solution, then with a NaCl saturated solution, dried over $Na_2SO_4$ and finally evaporated under vacuum at room temperature.

The product is purified by preparative TLC, eluting with ethyl ether/triethylamine 40/1. Rf=0,8.

The product is extracted from silica with chloroform/methanol=9,5/0,5 and it is obtained evaporating the solution under vacuum at room temperature. A colourless oil is obtained in a 35% yield (200 mg).

TLC: ethyl ether/triethylamine =40/1 Rf=0,8

MS; $^1H$- and $^{13}C$-NMR; field desorption, mike in conformity.

EXAMPLE 2

N-heptyl-geneserine.

A solution of the product obtained in example 1(c) (1,24 g) in 10 ml of acetone is treated with 14,7 ml of 6% hydrogen peroxide and a tip of $CaCO_3$. The reaction mixture is reacted shielded from light at room temperature for 55 hours, until the starting product disappears. Then acetone is evaporated off under nitrogen bubbling and the aqueous solution is extracted with 3×50 ml of ethyl ether.

The separated ether solution is washed with 10% $NaHCO_3$, then with a NaCl saturated aqueous solution, dried over $Na_2SO_4$ and evaporated under vacuum at room temperature to give a colourless oil which is the same as the product described in example 1(d) (TLC).

Yield=45% (600 mg)

EXAMPLE 3

N-heptyl-geneserine L-tartrate (CHF 2060).

To a solution of 0,400 g of the product obtained in example 2 or in example 3 in 11,2 ml of anhydrous degased isopropyl ether, a previously prepared solution of 0,160 g of L-tartaric acid in anhydrous degased isopropanol (3,2 ml ) is added. The reaction mixture is reacted until a clear solution is obtained, then 8 ml of anhydrous degased isopropyl ether are added and crystal formation starts. After other 2 hour stirring, the obtained solid is filtered, washing with some isopropyl ether.

Yield=60% (340 mg).

EXAMPLE 4

N-heptyl-geneserine salicylate.

A solution of 0,5 g of the product obtained in examples 1 and 2, in degased ethyl ether (15 ml) is added to a solution of salicylic acid (0,18 g) in 15 ml of degased ethyl ether, then the volume is left to decrease upon slow evaporation. After 48 hours, a white solid forms which is filtered and dried under vacuum at 30° C.

Yield=30% (200 mg).

EXAMPLE 5 a) Geneseroline.

To a solution of 1 g of geneserine in 70 ml of anhydrous degased ethanol, 10 mg of sodium are added under nitrogen atmosphere. The reaction mixture is heated to 40° C. and left under stirring at this temperature for 1 hour. When the reaction is over, solvent is evaporated off under vacuum at 30° C. The residue is treated with 10% HCl (40 ml) and extracted with chloroform (3×50 ml). The combined organic solutions are washed with a NaCl saturated aqueous solution, dried over sodium sulfate and evaporated under vacuum at room temperature to give a red oil, in an about 60% yield.

The oil is directly used for the subsequent reaction.

TLC: Ethyl acetate/Chloroform/Hexane 3/1/1 Rf=0,4.

b) N-heptyl-geneserine.

To a solution of 5 g of the product obtained in a) in 150 ml of anhydrous degased ethyl ether, 0,1 g of sodium are added and the reaction mixture is left to react for 1 hour at room temperature under nitrogen atmosphere. Then N-heptyl-imidazol-urea, obtained according to the example 1(b) (4,85 g), dissolved in 10 ml of anhydrous degased ethyl ether is added, during about 30 minutes. After a day at room temperature, the ether solution is washed with 100 ml of water, dried over sodium sulfate and evaporated under vacuum at 30° C. The obtained oil is purified by preparative TLC eluting with ethyl ether/triethylamine 40/1.

The product is extracted from silica with chloroform/ethanol 9,5/0,5, and it is obtained evaporating the solution under vacuum, at room temperature.

A colourless oil is obtained in a 50% yield (4 g).

TLC: Ethyl ether/Triethylamine 40/1 Rf=0,8.

EXAMPLE 6 a) Eseroline.

A solution of 10 g of eserine in 40 ml of 37% HCl is refluxed under stirring. After 2 hours the greenish solution is evaporated off under vacuum at 70° C. and the resulting oil is dissolved with 100 ml of water and treated with aq. ammonia to pH=5.

The solution is evaporated under vacuum at 70° C. to incipient precipitation, cooled and filtered. The obtained white solid is washed with acetone and ethyl ether, and dried under vacuum at 50° C. Yield 86% (8.0 g) as hydrochloride.

The base is obtained by addition of conc. aq. ammonia to an aqueous solution of the hydrochloride, saturation with NaCl and extraction with ethyl ether. The organic layer is dried over $Na_2SO_4$, filtered and evaporated under vacuum at 25° C., to obtain a white crystalline solid in a 80% yield (5.5 g).

b) N-Heptyleserine.

114 mg of sodium (50 wt % dispersion in paraffin) is added to a solution of 1.8 g of the product obtained according to a) in 100 ml of anhydrous ethyl ether, under nitrogen atmosphere. The mixture is allowed to stir to the complete dissolution, then a solution of 1.28 g of heptylisocianate in 30 ml of ethyl ether is added dropwise at room temperature. After one hour, $NH_4C_1$ (2 g) is added and the resulting mixture is stirred for half an hour, then washed with 30 ml of water; the organic layer is dried over $Na_2SO_4$, filtered and evaporated under vacuum at 25° C.

The resulting orange oil is purified by F.C. (eluent chloroform: 90=methanol: 10, stationary phase: silica gel, 30–60 um).

An oily product is obtained, in a 85% yield (2.5 g). Purity 95%.

c) N-Heptyl-geneserine.

To a solution of 2.44 g of the product obtained in b) in 100 ml of methylene chloride a solution of 2.93 g of m-chloroperbenzoic acid (Fluka) in 40 ml of methylene chloride is added at room temperature.

The solution is stirred for 30 min., then washed with 50 ml of a $NaHCO_3$ saturated solution and with 2×50 ml of a phosphate buffer (pH=3), The organic layer is dried over $Na_2SO_4$, filtered and evaporated under vacuum at room temperature. The resulting oil is extracted with 400 ml of n-hexane. The solvent is evaporated off under vacuum at 25° C. to give a colourless oil, which solidifies on standing. Yield=63% (1.6 g).

d) N-Heptyl-geneserine hydrochloride.

To a solution of 0.8 g of the product obtained in c) in 50 ml of ethyl ether a little excess of ethereal hydrochloric acid is added under stirring at 0° C. The resulting mixture is allowed to stir for an hour at 0° C., then is decanted and the viscous oil is dissolved in methylene chloride. The solution is evaporated under vacuum at room temperature to give a solid foam, which is stored in freezer.

Yield=80% (0.7 g)

TLC: Chloroform/methanol/formic acid 90/5/5 Rf=0.8

PHARMACOLOGICAL ACTIVITY

1. Acetylcholinesterase inhibition

The time course of inhibition of acetylcholinesterase (AchE) in the brain was assessed in male Crl:CD (SD) BR rats (Charles River Italia), weighing between 150–250 g.

The test substances were administered by s.c. route, dissolved in 2 ml/kg of sterile saline. 9 animals/group/time were used.

Controls received the vehicle only.

At various intervals (10–60–120–240 min) after administration the rats were sacrificed by decapitation and the brains were rapidly removed, weighed and immediately placed in 1 ml of phosphate buffer 0.1M, pH 8.0, added with 1% Triton 100 (Merck).

After homogenization and centrifugation at 19943 g for 15 min at 4° C. the surnatant was separated and used for the determination of AchE activity according to the acetyltiocholine method described by Ellmann (Ellman G. L. et al., Biochem. Pharmacol. 7, 88, 1961).

The activity concentrations obtained (U/l surnatant) were individually corrected for the brain weight.

TABLE 1

Brain acetylcholinesterase in the rat after treatment with CHF 2060 and the reference compounds.

| TREATMENT | Dose mg/kg s.c. | 10 min. U/l surn. | % inhib. | 60 min. U/l surn. | % inhib. |
|---|---|---|---|---|---|
| Vehicle | — | 3493 ± 214 | — | 3214 ± 202 | — |
| CHF 2060 | 9 | 3094 ± 197 | 11 | 2294 ± 150 | 29** |
|  | 27 | 3070 ± 117 | 12 | 1782 ± 164 | 45** |
| Vehicle | — | 3098 ± 181 | — | 2858 ± 199 | — |
| Geneserine tartrate | 3 | 1447 ± 100 | 53** | 1231 ± 86 | 57** |
| Vehicle | — | 2931 ± 262 | — | 3014 ± 228 | — |
| Physostigmine | 0.4 | 1368 ± 125 | 53** | 1483 ± 148 | 51** |
| Vehicle | — | 3153 ± 197 | — | 2544 ± 151 | — |
| Heptyl physostigmine tartrate | 1 | 2246 ± 115 | 29** | 1166 ± 85 | 54** |

| TREATMENT | Dose mg/kg s.c. | 120 min. U/l surn. | % inhib. | 240 min. U/l surn. | % inhib. |
|---|---|---|---|---|---|
| Vehicle | — | 3290 ± 170 | — | 2825 ± 208 | — |
| CHF 2060 | 9 | 2205 ± 171 | 33** | 1565 ± 80 | 45** |
|  | 27 | 1629 ± 38 | 50** | 914 ± 26 | 68** |

TABLE 1-continued

Brain acetylcholinesterase in the rat after treatment with CHF 2060 and the reference compounds.

| | | | | | |
|---|---|---|---|---|---|
| Vehicle | — | 3024 ± 75 | — | 2429 ± 160 | — |
| Geneserine tartrate | 3 | 2162 ± 134 | 28** | 2139 ± 208 | 12 |
| Vehicle | — | 2768 ± 185 | — | 2519 ± 148 | — |
| Physostigmine | 0.4 | 1829 ± 94 | 34** | 2234 ± 151 | 11 |
| Vehicle | — | 3168 ± 269 | — | 2935 ± 112 | — |
| Heptyl physostigmine tartrate | 1 | 1506 ± 115 | 52** | 1867 ± 52 | 36** |

Compounds were given by s.c. route, dissolved in 2 ml/kg of saline. Brains were homogenized in 2 ml of phosphate buffer 0.1 M, pH 8.0 added with 1% Triton 100. AchE activity was determined in the surnatant after centrifugation. Concentrations values were corrected for the brain weight. Statistical significance vs control ("t" Student's test):
*P = 0.05;
** P < 0.01

TABLE 2

Kinetic parameters of the inhibition of brain acetylcholinesterase in the rat after s.c. administration.

| TREATMENT | Dose mg/kg | T max | Max % inhib. | AUC 0–4 h % inib. hr |
|---|---|---|---|---|
| CHF 2060 | 9 | ≧240 min. | 45 | 127 |
| | 27 | ≧240 min. | 68 | 190 |
| Geneserine tartrate | 3 | 10–60 min. | 53–57 | 133 |
| Physostigmine | 0.4 | 10 min. | 53 | 135 |
| Heptyl physostigmine tartrate | 1 | 60 min. | 54 | 178 |
| | 0.3 | | | 94 |

Tmax = time of the maximal inhibition

2. Results

The brain AchE concentration values are shown in table 1, while the time course of the inhibition of the enzyme is depicted in FIG. 1.

A comparison between the kinetic parameters of the Ache inhibition is shown in table 2.

The results obtained indicate that CHF 2060 is a long-lasting inhibitor of brain AchE.

The effect appears to increase gradually during the 4 hrs following the treatment. A significant inhibition (29–45%; P<0,001) is found 1 hr after administration. Within 4 hrs of treatment the effect is increased over a factor of 1.5–1.6 in respect to those observed at the first hour.

Geneserine tartrate and physostigmine, at doses producing effects comparable (both in term of AUC and maximum inhibition) to those of 9 mg/kg CHF 2060, resulted in a more rapid effect, that peaks at 10–60 min., but it is reduced over a factor of 1.5–2 120 min. after the treatment. This effect disappears after 240 min.

Comparing the kinetics of the effects produced by the new Ache inhibitor Heptyl physostigmine tartrate (HPYS) with those obtained when administering CHF 2060 at a dose able to induce similar AUC "inhibition vs time" values (i.e. 1 vs 27 mg/kg), it is still evident that CHF 2060 exerts a more sustained action. In fact while the effect provoked by HPYS are reduced by a factor of 1.4 between 120 and 240 min, those observed after CHF 2060-treatment are increased by the same factor in the same time interval.

We claim:

1. A compound of formula I:

wherein R is a straight or branched $C_4$–$C_{12}$ alkyl group, an unsubstituted phenyl or benzyl group, or a phenyl substituted by a $C_1$–$C_4$ alkyl group, and a salt thereof with an organic or inorganic non-toxic acid.

2. The compound according to claim 1 wherein R is a straight $C_4$–$C_{12}$ alkyl group.

3. The compound according to claim 1 wherein R is n-heptyl or n-octyl.

4. The compound according to claim 1 wherein R is an unsubstituted benzyl or phenyl, or a phenyl substituted by a $C_1$–$C_2$ alkyl group.

5. The compound according to claim 1 which is a salt with tartaric, hydrochloric or salicylic acid.

6. A pharmaceutical composition containing as the active ingredient a compound according to claim 1 in admixture with a compatible carrier.

7. The method of treatment of a patient in need of a medicament having cholinesterase-inhibiting activity which consists of administering to said patient 10–1000 mgs daily of a compound of formula I wherein R is a straight or branched $C_4$–$C_{12}$ alkyl group, an unsubstituted phenyl or benzyl group, or a phenyl substituted by a $C_1$–$C_4$ alkyl group, and a salt thereof with an organic or inorganic non-toxic acid.

* * * * *